United States Patent [19]

Wilson

[11] Patent Number: 4,829,398
[45] Date of Patent: May 9, 1989

[54] APPARATUS FOR GENERATING AIR IONS AND AN AIR IONIZATION SYSTEM

[75] Inventor: Robert W. Wilson, Austin, Tex.

[73] Assignee: Minnesota Mining and Manufacturing Company, St. Paul, Minn.

[21] Appl. No.: 9,473

[22] Filed: Feb. 2, 1987

[51] Int. Cl.⁴ ............................................. H01T 19/00
[52] U.S. Cl. .................................... 361/213; 361/231
[58] Field of Search .............. 361/213, 229, 231, 235; 55/139; 422/22, 98, 83

[56] References Cited

U.S. PATENT DOCUMENTS

| | | | |
|---|---|---|---|
| 2,264,495 | 12/1941 | Wilner | 361/235 |
| 2,723,349 | 11/1955 | Rylsky | 361/231 |
| 2,785,312 | 3/1957 | Martin | 361/231 |
| 3,329,817 | 7/1967 | Walz | 250/493.1 |
| 3,711,743 | 1/1973 | Bolashy | 361/235 |
| 3,818,545 | 6/1974 | Olson et al. | 361/213 |
| 3,936,698 | 3/1976 | Meyer | 361/235 |
| 4,306,271 | 12/1981 | Weber | 361/235 X |
| 4,486,808 | 12/1984 | Cardone | 361/235 |
| 4,542,434 | 9/1985 | Gehlke et al. | 361/231 |

FOREIGN PATENT DOCUMENTS 842347  7/1981  U.S.S.R.

OTHER PUBLICATIONS

Secker, "A New Antistatic System With Long Range Throwing Power".
Blitshteyn et al, *Microcontamination*, vol. 3, No. 3 (1985) pp. 47–52 and p. 76.
Dunn, D., *Microcontamination*, vol. 3, No. 11 (1985), pp. 60–65.
Liu et al, "Characterization of Electronic Ionizers for Clean Rooms," *The Annual Meeting of the Institute of Environmental Sciences* (1985).

*Primary Examiner*—L. T. Hix
*Assistant Examiner*—D. Rutledge
*Attorney, Agent, or Firm*—Donald M. Sell; Walter N. Kirn; William D. Bauer

[57] ABSTRACT

An apparatus for generating air ions. Nuclear air ionizers are utilized which generate a multiplicity of ions of both positive and negative polarity by the bombardment of air molecules with radiation. An electric field is supplied in proximity to the nuclear air ionizers for generating an electrical field of alternating polarity near the source of generation of the multiplicity of ions. This combination creates waves of ions of opposite polarity which assist in moving the air ions away from the ionization source and preventing early recombination. An air ionization system for entire room or enclosure may be constructed utilizing a grid of a plurality of spaced apparatus as described above. Optionally, an air stream may be utilized to assist in moving the air ions created to a target surface.

20 Claims, 3 Drawing Sheets

APPARATUS FOR GENERATING AIR IONS AND AN AIR IONIZATION SYSTEM

BACKGROUND OF THE INVENTION

The present invention relates to air ionizers and ionization systems and more particularly to air ionizers and ionization systems intended for use as electrostatic eliminators.

In certain applications, it is very desirable to reduce or eliminate electrostatic charge buildup on surfaces of objects, sometimes referred to as a target surfaces. Examples are surfaces in a "clean room" where precision manufacturing and assembly occurs such as electronic integrated circuit or optical equipment fabrication. In a typical clean room, the air flow in the room is closely controlled. A laminar air flow from ceiling to floor is utilized to sweep contaminant particles down and out of a room while limiting the side-to-side movement of particles. In addition, a reduction or elimination of electrostatic charge on critical target surfaces leads to cleaner surfaces, i.e., to surfaces which attract fewer particulates. Further, a reduction or elimination of electrostatic charge on critical target surfaces reduces the possibility of such charge directly damaging or destroying electrical integrated circuits by electrostatic discharge. Electrostatic charge buildups can be reduced or prevented by the presence of ionized air near the critical target surface. The charged air molecules combine with electrostatic charges existing on the target surface eliminating or reducing them.

One known mechanism for creating ionized air molecules is the use of a nuclear radiation source. Minnesota Mining and Manufacturing Company of Saint Paul, Minn., assignee of the present application, manufactures and markets a line of nuclear static eliminators, e.g., model 205 spot source or model 210 bar source, based upon the creation of air ions by the high energy alpha particles emitted by polonium 210 called radionuclides. The radionuclides are contained in a multiplicity of ceramic beads which in turn are held in an epoxy resin. U.S. Pat. No. 3,329,817, Walz, entitled, Radiation Source, describes an exemplary nuclear radiation source which patent is hereby incorporated by reference. Nuclear air ionizers, by their very nature, produce a balance, i.e., an equal number, of ions of both positive and negative polarity.

One problem with alpha radiation based nuclear ionization sources is that the nuclear ionization source must be located very close to, i.e., within about 1.5 inches (3.81 centimeters) of, the surface to which it is to affect. While nuclear ionization sources operate very satisfactorily for many applications, e.g. a particular spot along a conveyor in an assemblyline process, in other applications they do not work as satisfactorily. For example, in a clean room environment, it is desirable that a large area, or volume of air be ionized. This is very difficult to achieve with nuclear air ionizers due to their requirement of being very close to the target surface. Alternatively, air ions must be directed to the target surface by an air stream, i.e. a fan, which is not desirable due in part to the possibility of the air stream dislodging contaminates from surfaces.

Another known mechanism for creating ionized air molecules is the use of electric ionizers. Electric ionizers utilize a needle, i.e., a sharp point, to which high voltage is connected. Examples of electrical ionizers include those described in U.S. Pat. No. 4,306,271, Weber; U.S. Pat. No. 3,936,698, Meyer; U.S. Pat. No. 3,711,743, Bolasny; and Russian Pat. No. 842,347. Further, U.S. Pat. No. 4,542,434, Gehlke et al, entitled, Method and Apparatus for Sequenced Bipolar Air Ionization, describes an electrical air ionizer with two spaced electrodes, one of which is connected to a pulsed positive high voltage generator and the other to a pulsed negative high voltage generator.

Electrical air ionizers can produce large quantities of ions in a short period of time. However, experiments have shown that electrical ionizers tend to lead toward an unbalanced state, i.e., more ions of one polarity than another, which can actually cause electrostatic buildup instead of preventing it. This problem is described in an article by Blitshteyn, M. and Shelton, S., *Microcontamination*, Vol. 3, No. 3, pages 47–52, 76 (1985). Further, degradation of the needles, or electrodes, over a period of time also can lead to particulate contamination. This is described in an article by Liu, B., Pui, D., Kinstley, W., and Fisher, W., "Characterization of Electronic Ionizers for Clean Rooms" presented at *The Annual Meeting of the Institute of Environmental Sciences*, 1985.

U.S. Pat. No. 2,723,349, Rylsky, entitled, Apparatus For Ionizing an Air Stream, describes an apparatus which utilizes an air stream and provides for the generation of primarily only negative ions for therapeutic purposes (condition of general well-being). The system in Rylsky involves generation of ions by the use of radium (nuclear) emmissions which generates ions of both positive and negative polarity. A high direct current potential is applied to the ionizing structure to make it a negative potential, thus, neutralizing positive ions generated by the radium and leaving only "desirable" negative ions. Note that Rylsky does not show or suggest an alternating high voltage source but only the direct current source. In column 3 at lines 38–46, Rylsky does teach that a direct current voltage of the opposite, i.e., positive, potential could be utilized if it were desired to allow positive ions to exist in the air stream. While Rylsky does suggest the use of either applying a positive potential for a negative potential to the ionizing structure he does not show, teach or suggest both polarities alternately.

U.S. Pat. No. 2,785,312, Martin, Jr., entitled Ion Generator Using Radioactive Material, describes an apparatus which is quite similar to Rylsky but which utilizes a polonium nuclear ion source. In column 3 at lines 36–47, Martin, Jr. suggests the connection of an electric potential of either potential, but not both to the ionizing structure. Again, as in Rylsky, the object of Martin, Jr. is to generate ions of primarly only of one polarity.

An article by Secker, "A New Antistatic System With Long Range Throwing Power", Industrial Applications Society, IEE-IAS Annual Meeting, Toronto, Ontario (Oct. 1–5, 1978) compares the range of radioactive powered antistatic bars with conventional electrical antistatic bars. Secker contains no suggestion of combining radioactive sources with electrical fields or sources.

Other ionizers are described in U.S. Pat. No. 3,711,743 which describes a single ionizing electrode which is switched between positive and negative high voltage states. Also, U.S. Pat. No. 2,264,495 teaches the switching of a single ionizing electrode between positive and negative ion generation in response to sensors which detect variations in concentrations of both types of ions of incoming air in order to maintain a predetermined ratio of positive and negative ions.

SUMMARY OF THE INVENTION

The present invention combines a nuclear ionizing source with an electrical field assist to quickly disperse ions created by the nuclear generator. Unlike prior art electrical ionizers, the high voltage utilized in the present invention creates an electric field which, when periodically reversed in polarity, will disperse waves of ions generated by the nuclear ion generator. Further, by separating positive and negative ions into spatially separate waves, the recombination of such positive and negative ions with each other can be minimized. Since recombination of ions is minimized, the lifetime of such ions is increased which effectively increases the range of effectiveness of the ionizing sources. An increase in the lifetime of ions allows a greater time for ions to be moved, either by an electric field, by an air stream, or both, farther distances. The present invention greatly expands the distance at which electrostatic charge elimination or reduction will be effective. Even so, optionally the nuclear ionizer with the electric field potential could also be utilized with an air stream assist to even further expand the satisfactory range of operation.

The present invention provides an apparatus for generating air ions. An ionization device is provided for generating by bombardment of air molecules with radiation a multiplicity of ions of both positive and negative polarity. An electrical device which cooperates with the ionization device generates an electrical field of alternating polarity near the source of generation of the multiplicity of ions. Constructed in this manner, waves of ions of opposite polarity are created which assists in moving the air ions away from the ionization apparatus, thus, effectively increasing the range of electostatic elimination or reduction of the air ionizer. Preferably, the electrical device is an electrically conductive object positioned in proximity with the ionization device. With an electrical power supply producing a series of alternating polarity voltage pulses and a coupling device connected to the electrical power supply and the electrically conductive object for coupling the series of alternating polarity voltage pulses from the electrical power supply to the electrically conductive object. Preferably the ionization device includes a nuclear ionization source and also preferably the ionization device operates with alpha radiation. Preferably, the series of alternating polarity voltage pulses are of substantially equal voltage magnitude and preferably are of substantially equal time duration. Preferably, the series of all the alternating polarity voltage pulses has a frequency which is high enough to prevent undesired charge and recharge of an object in the path of the air ions and which is low enough to allow the air ions to be moved away from the electrically conductive object. Preferably, the series of alternating polarity voltage pulses have a frequency of about 0.05 Hertz to about 5 Hertz. Optionally, an air flow mechanism can be utilized in proximity with the ionization device and the electrical device for providing a desired flow of air in the path of the the air ions to assist in their spatial distribution.

A grid of ion generating apparatus as described in this application could be utilized in a room, hood or other enclosure to form an ionization system. Such a system allows for effective electrostatic charge neutralization where none heretofor has existed. Effectively, an entire working area within a clean room, hood or other enclosure can be treated allowing for cleaner surfaces and better precision optical instruments and integrated circuits to be fabricated. Since integrated circuit density is foremost in integrated circuit fabrication, use of the present invention may allow even greater densities of integrated circuits to be fabricated due to the cleaner surfaces and less contamination.

An air ionization system could be utilized advantageously in a "non-clean" room or enclosure in order to limit electrostatic discharge.

The present invention provides for an air ionization system. A grid of a plurality of spaced apparatus for generating air ions is provided. Each of the apparatus for generating air ions utilizes an ionization device for generating by bombardment of air molecules with radiation a multiplicity of ions of both positive and negative polarity. Each apparatus also utilizes an electrical device cooperating with the ionization device for generating an electrical field of alternating polarity near the source of generation of the multiplicity of ions. In this manner, each of the apparatus for generating air ions creates waves of ions of opposite polarity which assist in moving the air ions away from the ionization device. The grid of a plurality of spaced air ion generators creates an effective room, hood or other enclosure air ionization system.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
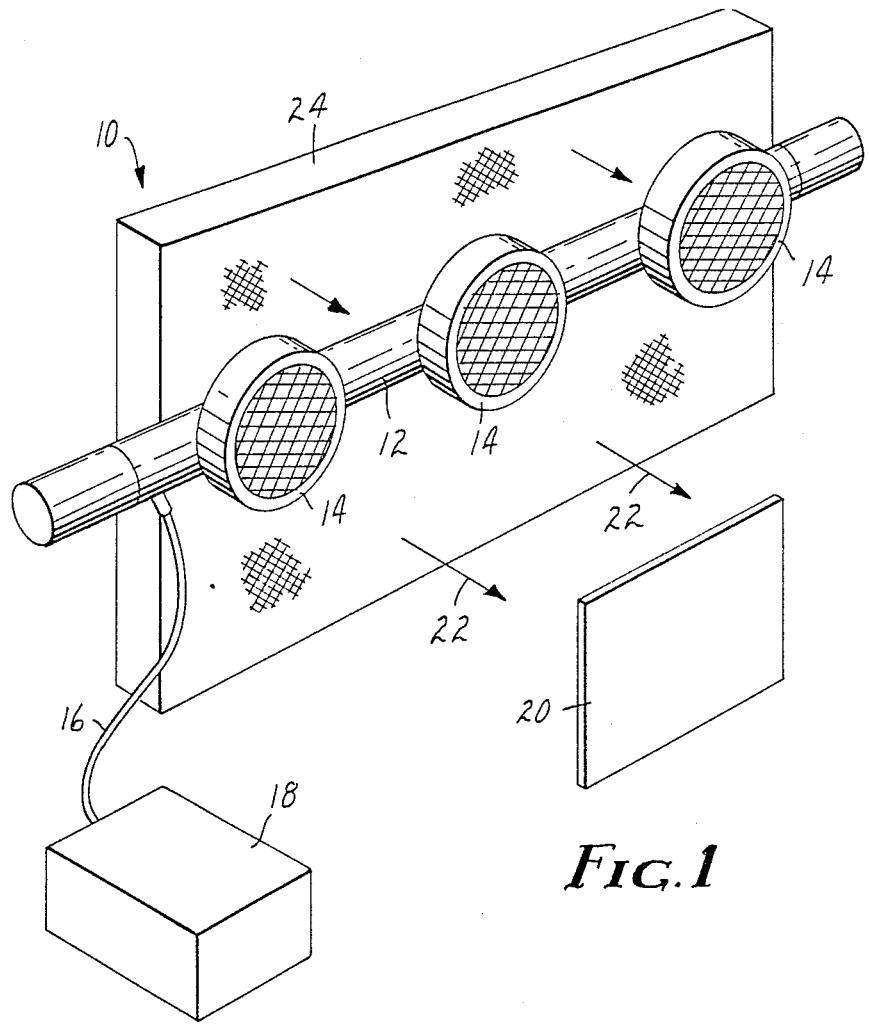
FIG. 1 is a perspective view of the present invention in conjunction with an air stream, associated filter and a target surface.

FIG. 1 illustrates a perspective view of an apparatus 10 for generating air ions according to the present invention. A mounting bar 12 holds at least one nuclear air ionizer 14. Such a nuclear air ionizer generates a multiplicity of ions of both positive and negative polarity by the bombardment of air molecules with radiation, particularly, alpha radiation. Such nuclear air ionizers are preferably one of several of a line of nuclear static eliminators manufactured by Minnesota Mining and Manufacturing Company, Saint Paul, Minn., assignee of the present application, which utilize high energy alpha particles emmitted by polonium 210 called radionuclides. The radionuclides are contained in a multiplicity of ceramic beads which in turn are held in an epoxy resin. Preferably, either the model 205 spot source nuclear static eliminator or model 210 bar source nuclear static eliminator may be utilized. U.S. Pat. No. 3,329,817, Walz, entitled, Radiation Source, which has already been incorporated by reference describes an exemplary nuclear radiation source. Nuclear air ionizers 14, by their very nature, produce a balance of ions of both positive and negative polarity. Cooperating in close proximity with the nuclear air ionizers 14 is an electrical source for generating an electrical field of alternating polarity. In a preferred embodiment, the cases of the nuclear air ionizers 14 are constructed of a metallic, i.e., electrically conductive, material. Thus, the electrically conductive cases of nuclear air ionizers 14 are connected via cable 16 to a power supply 18. Power supply 18 supplies to the electrically conductive cases of nuclear air ionizers 14 an alternating relatively high voltage which, although not generating a significant number of ions itself, does create an electric field near nuclear air ionizers 14 of alternating polarity according to the polarity of the voltage supplied to it by power supply 18. Nuclear air ionizers 14 are producing a balanced supply of ions, that is, a relatively equal number of ions of both positive and negative polarity. When power supply 18 creates a positive voltage potential on the cases of nuclear air ionizers 14, ions of a negative polarity produced by nuclear air ionizers 14 will be quickly attracted to the cases of nuclear air ionizers 14 and absorbed, i.e., neutralized. Since the ions of negative polarity generated by nuclear air ionizers 14 have been eliminated, there remains a region of positive air ions remaining which have been generated by nuclear air ionizers 14. Since the cases of nuclear air ionizers 14 are still charged to a positive potential, this region of positive air ions is repelled from the cases of nuclear air ionizers 14 toward target surface 20. After a sufficient period, power supply 18 reverses the polarity of the electric potential supplied to the cases of nuclear air ionizers 14, namely supplying a relatively high voltage with a negative potential. The negatively charged cases of nuclear air ionizers 14 will attract and neutralize positive air ions generated by nuclear air ionizers 14 leaving a region of negatively charged air ions. The region of negatively charged air ions will again be repelled away from the cases of nuclear air ionizers 14 due to their like polarity. As the reversal in polarity of the charge on the cases of nuclear air ionizers 14 is continued, repeated regions, or waves, alternating in polarity by wave, are repelled away from the cases of nuclear air ionizers 14 toward target surface 20. Optionally, FIG. 1 illustrates the apparatus for generating air ions 10 to be utilized with an air stream 22 in order to help propel the waves of air ions to target surface 20. If an air stream 22 is utilized in conjunction with the apparatus for generating air ions, it is preferred that a filter 24 be utilized in order to keep the air stream 22 as free from contaminates as possible.

Figure 2:
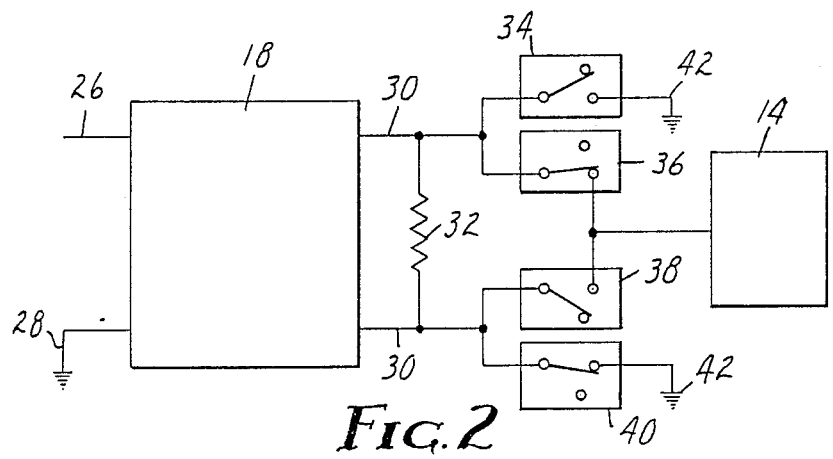
FIG. 2 is a block diagram of the electrical aspects of the present invention.
Figures 3, 4:
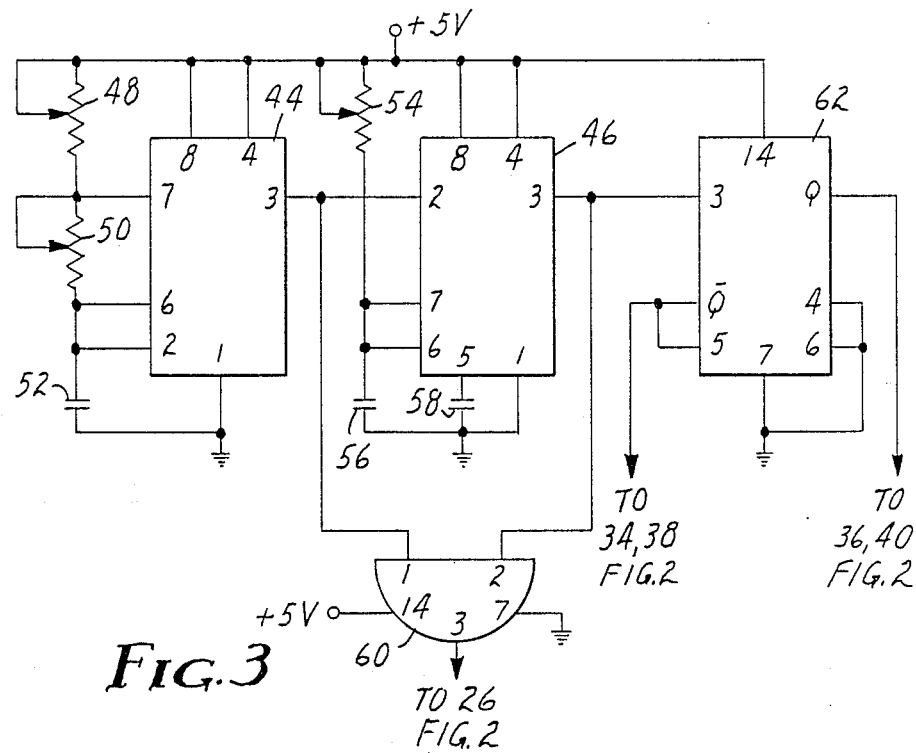
FIG. 3 is a schematic diagram of the timer utilized in the present invention.
FIG. 4 are logic waveforms utilized in the present invention.
Figure 5:
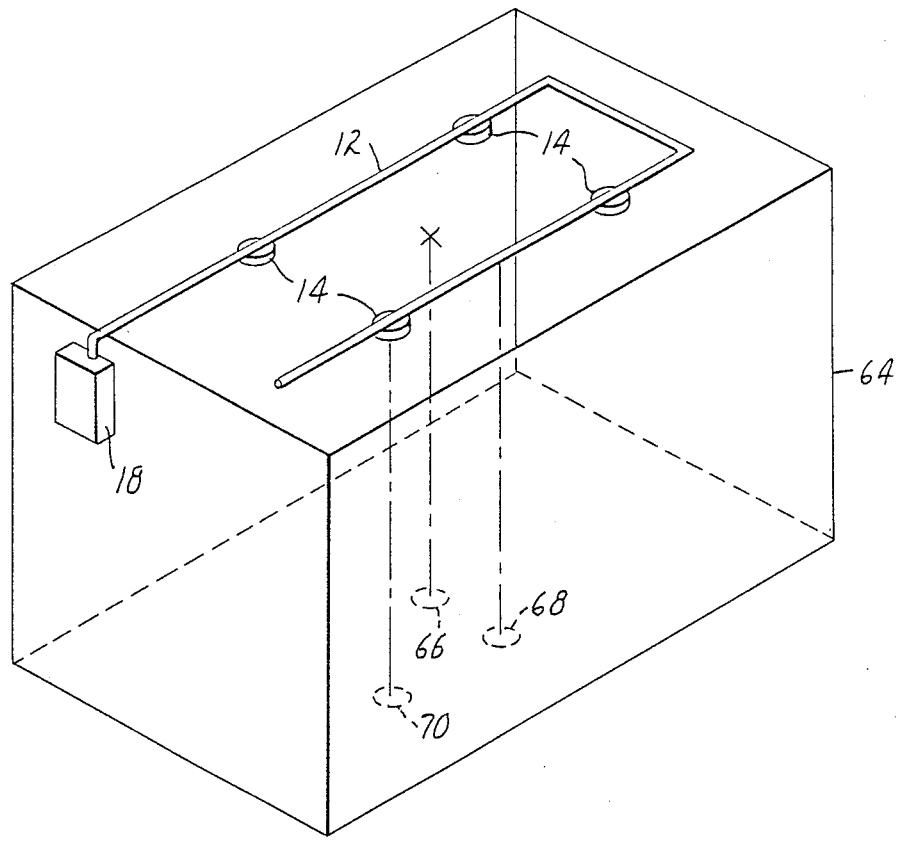
FIG. 5 is a perspective view of an exemplary room air ionization system.

FIG. 2 illustrates power supply 18 which is connected to a relatively low voltage 26, namely, five volts direct current. The output of power supply 18 provides a high voltage output 30 of approximately 1,200 volts. The high voltage output 30 is coupled across a load resistor 32 to high voltage relays 34, 36, 38 and 40. Relays 34 and 36 are connected into one leg of high voltage output 30 so that that side of high voltage output 30 is connected alternatively to electrical ground 42 or to the cases of nuclear air ionizers 14 where it generates the needed electrical field. Similarly, the opposite leg of high voltage output 30 is connected alternatively through relays 38 and 40 so that that leg is connected alternatively to the cases of nuclear air ionizers 14 or electrical ground 42, respectively. Relays 34, 36, 38 and 40 are controlled by a controlling circuit illustrated in FIG. 3. As illustrated in FIG. 3, two 555 timer circuits 44 and 46 to produce waveforms 110 and 112 illustrated in FIG. 4. Resistors 48, 50 and capacitor 52 are utilized in conjunction with timer circuit 44. Resistor 54 and capacitors 56 and 58 are utilized in conjunction with timer circuit 46. The output of timer circuit 44 and the output of timer circuit 46 go to AND gate 60 whose output is applied to the low voltage input 26 of power supply 18 of FIG. 2. The output of timer circuit 46 is supplied to the input of Type D flip-flop 62 whose output produces the waveform 114 illustrated in FIG. 5. The output of AND circuit 60 is shown in the waveform 116 of FIG. 4. Connected in this manner, the controller circuit of FIG. 3 operates in conjunction with power supply 18 to control relays 34, 36, 38 and 40 to supply an alternating high voltage source of potential to the cases of nuclear air ionizers 14, located in proximity to the nuclear air ionizers 14. The components utilized in FIG. 2 and 3 preferably have the following values/identifications:

| Reference No. | Model/Value | Manufacturer |
| --- | --- | --- |
| 18 | Floating LV/HV Power Supply | Venus Scientific |
| 32 | 22 Megohms | |
| 34 | 183RE1A3G-5G | Sigma |
| 36 | 183RE1A3G-5G | Sigma |
| 38 | 183RE1A3G-5G | Sigma |
| 40 | 183RE1A3G-5G | Sigma |
| 44 | LM555 | National Semiconductor |
| 46 | LM555 | National Semiconductor |
| 48 | 1 Megohm Potentiometer | |
| 50 | 1 Megohm Potentiometer | |
| 52 | 10 Microfarads | |
| 54 | 1 Megohm Potentiometer | |
| 56 | 10 Microfarads | |
| 58 | 0.01 Microfarads | |
| 60 | AND SN7408 | Texas Instruments |
| 62 | SN74LS74 | Texas Instruments |

In FIG. 4, waveform 114 is the Q output of flip-flop 62 which is supplied to relays 36 and 40. The logical antithesis of waveform 114 is supplied to relays 34 and 38. Time 118 in FIG. 4 is determined by multiplying 0.693 times the value of capacitor 52 times the sum of the resistances of resistors 48 and 50. Time 120 in FIG. 4 is determined by multiplying 0.693 times the value of resistor 50 times the value of capacitor 52. Time 122 in FIG. 4 is determined by multiplying 0.693 times the value of resistor 54 and the value of capacitor 56.

In one exemplary embodiment of the present invention, the apparatus for generating air ions was directed toward the area where charge neutralization was required. This apparatus was positioned at various distances from a charged plate ion flux monitor that consisted of a 6 inch (15 centimeter) by 6-inch (15 centimeter) square plate connected to a very high impedance volt meter. The plate and volt meter combination had a capacitance of 20 picofarads. The plate was charged to 1,000 volts and the decay of the voltage was monitored and recorded on a chart recorder. An indication of the efficiency of the ionizer is the time required for the voltage to drop to 100 volts, with shorter times indicating a more efficient neutralizer. The results of this configuration are shown in Table I. Also shown in Table I is the voltage swing occurring on the plate after it has been neutralized to zero volts, which is an indication of the surface charging due to the waves of ions being received by the plate.

TABLE I

| Distance (Inches) | Pulse Voltage (+ or −) (Volts) | Frequency (Hertz) | Neutralization Time (Seconds) | Voltage Swing (Volts) |
|---|---|---|---|---|
| 18 | 1100 | 1 | 144 | 10 |
| 18 | 1100 | .5 | 82 | 20 |
| 18 | 1100 | .25 | 36 | 25 |
| 18 | 1100 | .125 | 33 | 50 |
| 18 | 1100 | .0625 | 22 | 75 |
| 10 | 1100 | 1 | 12 | 20 |
| 13 | 250 | 1 | 156 | — |
| 13 | 500 | 1 | 52 | 5 |
| 13 | 750 | 1 | 38 | 10 |
| 13 | 1000 | 1 | 30 | 20 |
| 13 | 1250 | 1 | 22 | 30 |
| 13 | 1500 | 1 | 16 | 40 |

In another application, an entire room air ionization system was created to supply coverage to an entire clean room. Four nuclear air ionizers 14 were utilized positioned in room 64. The cases of the nuclear air ionizers 14 were connected via a coupling device to power supply 18. Thus, a grid of a plurality of space nuclear air ionizers was positioned within the clean room 64. The four nuclear air ionizers were hung in a rectangular pattern 7 inches (18 centimeters) below air filters (not shown in FIG. 5) in the clean room 64. The sides of the rectangle were 64 (163 centimeters) by 54 inches (137 centimeters). A charged plate ion flux monitor, described above, was placed 5 feet (1.5 meters) below the nuclear air ionizers at three locations 66, 68 and 70. Location 66 is at the center of the rectangle, location 68 is midway between two of the nuclear air ionizers 14 and location 70 was directly beneath one of the nuclear air ionizers 14. Air flow within the clean room 64 was from ceiling to floor and was measured as 110 feet per minute (56 centimeters per second) at the face of the filters (not shown). Voltage decay measurements were made at each of the locations for two different pulse lengths. The results are supplied in Table II.

TABLE II

| Position | Distance Below (Feet) | Voltage (+ or −) | Pulse Length (Seconds) | Neutralization Time (Seconds) |
|---|---|---|---|---|
| 66 | 3 | 1000 | 6 | 135 |
| 66 | 4 | 1000 | 6 | 105 |
| 66 | 5 | 1000 | 6 | 99 |
| 68 | 3 | 1000 | 6 | 105 |
| 68 | 4 | 1000 | 6 | 93 |
| 68 | 5 | 1000 | 6 | 75 |
| 70 | 3 | 1000 | 6 | 14 |
| 70 | 4 | 1000 | 6 | 24 |
| 70 | 5 | 1000 | 6 | 35 |
| 66 | 3 | 1250 | 6 | 93 |
| 66 | 4 | 1250 | 6 | 75 |
| 66 | 5 | 1250 | 6 | 81 |
| 68 | 3 | 1250 | 6 | 63 |
| 68 | 4 | 1250 | 6 | 63 |
| 68 | 5 | 1250 | 6 | 59 |
| 70 | 3 | 1250 | 6 | 21 |
| 70 | 4 | 1250 | 6 | 25 |
| 70 | 5 | 1250 | 6 | 43 |
| 66 | 3 | 1500 | 6 | 63 |
| 66 | 4 | 1500 | 6 | 69 |
| 66 | 5 | 1500 | 6 | 66 |
| 68 | 3 | 1500 | 6 | 63 |
| 68 | 4 | 1500 | 6 | 48 |
| 68 | 5 | 1500 | 6 | 60 |
| 70 | 3 | 1500 | 6 | 16 |
| 70 | 4 | 1500 | 6 | 24 |
| 70 | 5 | 1500 | 6 | 43 |
| 66 | 3 | 1250 | 3 | 105 |
| 66 | 4 | 1250 | 3 | 81 |
| 66 | 5 | 1250 | 3 | 69 |
| 68 | 3 | 1250 | 3 | 69 |
| 68 | 4 | 1250 | 3 | 63 |
| 68 | 5 | 1250 | 3 | 69 |
| 70 | 3 | 1250 | 3 | 13 |
| 70 | 4 | 1250 | 3 | 18 |
| 70 | 5 | 1250 | 3 | 32 |
| 66 | 3 | 1500 | 3 | 93 |
| 66 | 4 | 1500 | 3 | 69 |
| 66 | 5 | 1500 | 3 | 60 |
| 68 | 3 | 1500 | 3 | 63 |
| 68 | 4 | 1500 | 3 | 42 |
| 68 | 5 | 1500 | 3 | 60 |
| 70 | 3 | 1500 | 3 | 12 |
| 70 | 4 | 1500 | 3 | 18 |
| 70 | 5 | 1500 | 3 | 30 |

A preferred pulsing frequency, i.e., the preferred rate at which the polarity of the electrical field is reversed has been determined. Measurements were made in a horizontal laminar flow clean hood at an air flow velocity of 100 feet per minute (51 centimeters per second) using a mounting bar 12 with two nuclear air ionizers 14 spaced 10 inches, (25 cm) apart. Voltage pulses of positive and negative 1,200 volts were applied to the cases of nuclear air ionizers 14. The results obtained are described in Table III.

TABLE III

| Pulse Frequency (Hertz) | Distance (Inches) | Neutralization Time (Seconds) | Voltage Swing (Volts) |
|---|---|---|---|
| 0.125 | 13 | 1** | 400 |
| 0.25 | 13 | 1** | 250 |
| 0.5 | 13 | 2 | 175 |
| 1.0 | 13 | 2 | 100 |
| 2.0 | 13 | 2.4 | 30 |
| 4.0 | 13 | 2.7 | 5 |
| 10 | 13 | 5.1 | — |
| 20 | 13 | 8.4 | — |
| 0.125 | 18 | 1** | 200 |
| 0.25 | 18 | 2** | 150 |
| 0.5 | 18 | 3 | 100 |
| 1.0 | 18 | 3.6 | 50 |
| 2.0 | 18 | 3.9 | 15 |
| 4.0 | 18 | 4.8 | 5 |
| 10 | 18 | 9.9 | — |
| 20 | 18 | 15.9 | — |

**Where the cycle times are the same as or longer than the neutralization times, these times are approximate.

As can be seen from Table III, it appears that the preferred frequency range is from 0.5 Hertz to 4 Hertz. This preferred frequency occurs only in an apparatus for generating air ions used in a laminar flow hood with an air flow of 100 feet per minute (51 centimeters per second). For use at greater distances such as in the case of a whole room air ionizer, the optimum frequency is lower in the range of 0.05 Hertz to 0.5 Hertz. Thus, the preferred range of frequency of reversal of electric field is in the range of 0.05 Hertz to 4 Hertz.

Thus, there has been shown and described a novel apparatus for generating air ions and an air ionization system. It is to be recognized and understood, however, that various changes modifications and substitutions may be made in the form and details of the present invention without departing from the scope of the following claims:

What is claimed is:

1. An apparatus for generating air ions, comprising:

ionization means for generating by bombardment of air molecules with radiation from a nuclear ionization source a multiplicity of ions of both positive and negative polarity; and electrical means, cooperating with said ionization means, for generating an electrical field of alternating polarity near the source of generation of said multiplicity of ions;

whereby waves of ions of opposite polarity are created which assists in moving said air ions away from said ionization means.

2. An air ionization system, comprising:

a grid of a plurality of spaced apparatus for generating air ions;

wherein each of said apparatus for generating air ions comprises:

ionization means for generating by bombardment of air molecules with radiation from a nuclear ionization source a multiplicity of ions of both positive and negative polarity; and electrical means, cooperating with said ionization means, for generating an electrical field of alternating polarity near the source of generation of said multiplicity of ions;

whereby waves of ions of opposite polarity are created which assists in moving said air ions away from said ionization means.

3. An apparatus for generating air ions, comprising:

ionization means for generating by bombardment of air molecules with radiation a multiplicity of ions of both positive and negative polarity; and electrical means, cooperating with said ionization means, for generating an electrical field of alternating polarity near the source of generation of said multiplicity of ions;

wherein said electrical means comprises an electrically conductive object positioned in proximity with said ionization means; an electrical power supply producing a series of alternating polarity voltage pulses; and coupling means, connected with said electrical power supply and said electrically conductive object, for coupling said series of alternating polarity voltage pulses from said electrical power supply to said electrically conductive object; and wherein said ionization means comprises a nuclear ionization source;

whereby waves of ions of opposite polarity are created which assists in moving said air ions away from said ionization means.

4. An apparatus as in claim 3 wherein said ionization means operates with alpha radiation.

5. An apparatus as in claim 3 wherein said series of alternating polarity voltage pulses are of substantially equal voltage magnitude.

6. An apparatus as in claim 3 wherein said series of alternating polarity voltage pulses has a frequency which is high enough to prevent undesired charge and recharge of an object in the path of said air ions and which is low enough to allow said air ions to be moved away from said electrically conductive object.

7. An apparatus as in claim 3 which further comprises air flow means, in proximity with said ionization means and said electrical means, for providing a desired flow of air in the path of said air ions to assist in their special distribution.

8. An apparatus as in claim 7 wherein said air flow means is a fan.

9. An apparatus for generating air ions, comprising:

ionization means for generating by bombardment of air molecules with radiation a multiplicity of ions of both positive and negative polarity; and electrical means, cooperating with said ionization means, for generating an electrical field of alternating polarity near the source of generation of said multiplicity of ions;

wherein said electrical means comprises an electrically conductive object positioned in proximity with said ionization means; an electrical power supply producing a series of alternating polarity voltage pulses; and coupling means, connected with said electrical power supply and said electrically conductive object, for coupling said series of alternating polarity voltage pulses from said electrical power supply to said electrically conductive object;

wherein said series of alternating polarity voltage pulses are of substantially equal voltage magnitude;

wherein the time duration of positive pulses from said alternating polarity voltage pulses are substantially equal to the time duration of negative pulses from said alternating polarity voltage pulses; and wherein said series of alternating polarity voltage pulses have a frequency of from about 0.05 Hertz to about 4 Hertz;

whereby waves of ions of opposite polarity are created which assists in moving said air ions away from said ionization means.

10. An apparatus as in claim 9 wherein said electrically conductive object is a case containing said nuclear ionization source.

11. An apparatus as in claim 10 wherein said series of alternating polarity voltage pulses are trapezoidal waves with no off time between said alternating polarity voltage pulses.

12. An air ionization system, comprising:

a grid of a plurality of spaced apparatus for generation air ions;

wherein each of said apparatus for generating air ions comprises:

ionization means for generation by bombardment of air molecules with radiation a multiplicity of ions of both positive and negative polarity; and electrical means, cooperating with said ionization means, for generating an electrical field of alternating polarity near the source of generation of said multiplicity of ions;

wherein said electrical means comprises an electrically conductive object positioned in proximity with said ionization means; an electrical power supply producing a series of alternating polarity voltage pulses; and coupling means, connected with said electrical power supply and said electrically conductive object, for coupling said series of alternating polarity voltage pulses from said electrical power supply to said electrically conductive object; and wherein said ionization means comprises a nuclear ionization source;

whereby waves of ions of opposite polarity are created which assists in moving said air ions away from said ionization means.

13. An air ionization system as in claim 12 wherein said ionization means operates with alpha radiation.

14. An air ionization system as in claim 12 wherein said series of alternative polarity voltage pulses are of substantially equal voltage magnitude.

15. An air ionization system as in claim 14 wherein the time duration of positive pulses from said alternating polarity voltage pulses are substantially equal to the time duration of negative pulses from said alternating polarity voltage pulses.

16. An air ionization system as in claim 15 wherein said series of alternating polarity voltage pulses has a frequency which is high enough to prevent undesired charge and recharge of an object in the path of said air ions and which is low enough to allow said air ions to be moved away from said electrically conductive object.

17. An air ionization system as in claim 12 which further comprises at least one air flow means, operating in conjunction with said grid, for providing a laminar flow of air in the path of at least some of said air ions to assist them in their spacial distribution.

18. An air ionization system, comprising:
a grid of a plurality of spaced apparatus for generating air ions;
wherein each of said apparatus for generating air ions comprises:
ionization means for generating by bombardment of air molecules with radiation a multiplicity of ions of both positive and negative polarity; and
electrical means, cooperating with said ionization means, for generating an electrical field of alternating polarity near the source of generation of said multiplicity of ions;
wherein said electrical means comprises an electrically conductive object positioned in proximity with said ionization means; an electrical power supply producing a series of alternating polarity voltage pulses; and coupling means, connected with said electrical power supply and said electrically conductive object, for coupling said series of alternating polarity voltage pulses from said electrical power supply to said electrically conductive object;
wherein said series of alternative polarity voltage pulses are of substantially equal voltage magnitude;
wherein the time duration of positive pulses from said alternating polarity voltage pulses are substantially equal to the time duration of negative pulses from said alternating polarity voltage pulses; and
wherein said series of alternating polarity voltage pulses have a frequency of from about 0.05 Hertz to about 4 Hertz;
whereby waves of ions of opposite polarity are created which assists in moving said air ions away from said ionization means.

19. An air ionization system as in claim 18 wherein said electrically conductive object is a case containing said nuclear ionization source.

20. An air ionization system as in claim 19 wherein said series of alternating polarity voltage pulses are trapezoidal waves with no off time between said alternating polarity voltage pulses.

* * * * *

UNITED STATES PATENT AND TRADEMARK OFFICE
CERTIFICATE OF CORRECTION

PATENT NO. : 4,829,398

DATED : May 9, 1989

INVENTOR(S) : Robert W. Wilson

It is certified that error appears in the above-identified patent and that said Letters Patent is hereby corrected as shown below:

Col. 9, line 65, "special" should read --spacial--.

Signed and Sealed this

Third Day of October, 1989

*Attest:*

DONALD J. QUIGG

*Attesting Officer*      *Commissioner of Patents and Trademarks*